US00PP12415P2

(12) United States Plant Patent
McLaren

(10) Patent No.: US PP12,415 P2
(45) Date of Patent: Feb. 19, 2002

(54) APPLE TREE NAMED 'NEVSON'

(75) Inventor: John McLaren, Alexandra (NZ)

(73) Assignee: Nevis Fruit Company LTD, Cromwell (NZ)

( * ) Notice: Subject to any disclaimer, the term of this patent is extended or adjusted under 35 U.S.C. 154(b) by 0 days.

(21) Appl. No.: 09/488,946

(22) Filed: Jan. 18, 2000

(51) Int. Cl.[7] ..... A01H 5/00

(52) U.S. Cl. ..... Plt./161

(58) Field of Search ..... Plt./161, 162, 171

(56) References Cited

PUBLICATIONS

UPOV–ROM GTITM Computer Database, 2000/06, GTI Jouve Retrieval Software, citation for 'Nevson'.*

* cited by examiner

*Primary Examiner*—Bruce R. Campell
*Assistant Examiner*—Susan B. McCormick
(74) *Attorney, Agent, or Firm*—Wells, St. John, Roberts, Gregory & Matkin, P.S.

(57) ABSTRACT

A new and distinct variety of apple tree (*Malus Pumila Mill*) named 'Nevson,' and which is characterized as to novelty by uniqueness of shape, color, flavor and texture, and a date of maturity for commercial harvesting and shipment of approximately September 10 through October 1 under the ecological conditions prevailing in the Columbia Basin area of Central Washington.

3 Drawing Sheets

BACKGROUND OF THE INVENTION

The present invention relates to a new and distinct variety of apple tree named 'Nevson' and more particularly to an apple tree which bears an attractive predominantly red and yellow-skinned apple which has a crisp, fine grained texture, and a well balanced flavor.

ORIGIN AND ASEXUAL REPRODUCTION OF THE NEW VARIETY

It has long been recognized that an important factor contributing to the success of any variety of apple tree bearing fruit for the fresh market is its respective date of harvesting in relative comparison to other varieties bearing similar fruit in the same season. The new variety 'Nevson' is noteworthy, as noted above, in producing an attractively colored fruit which is ripe for harvesting and shipment at approximately the same time as the 'Gala' apple cultivar under the same ecological conditions prevailing in the Columbia Basin area of south central Washington State.

The new and distinct variety of apple tree ('*Malus Pumila Mill*') was a controlled cross-pollination in 1979 of a 'Gala' ('Kidd's D8' U.S. Plant Pat. No. 3,637) and 'Red Delicious' ('Hawkes Bay Red'—not patented) then growing on the inventor's property which is located near Alexandra, New Zealand. The inventor noted the promising characteristics of this new 'Gala' and 'Red Delicious' cross, and in 1986, removed bud wood of the new seedling and grafted it into test trees then growing on the same property. These test trees have been subsequently studied and it has been determined that the same desirable characteristics observed in the original seedling were expressed in the test trees. Additionally, the fruit produced from these trees has been compared and contrasted with the fruit produced from the original seedling, and it has been confirmed that this asexual propagation resulted in an apple tree being produced which possesses the same distinctive characteristics as the original controlled cross pollinated seedling.

SUMMARY

The 'Nevson' apple tree is characterized principally as to novelty by producing an attractively colored fruit which is ripe for harvesting and shipment approximately 10 September through 1 October under the ecological conditions prevailing in the Columbia Basin area of central Washington. This date of harvesting is approximately the same as the 'Gala' cultivar growing at the same location. The present variety is easily distinguishable from the fruit produced by the 'Red Delicious' and 'Gala' cultivars that are its parents, in that, it has a unique elongated shape and attractive coloring.

DETAILED DESCRIPTION OF THE DRAWING

The accompanying drawings are color photographs of the present variety.

On Sheet 1, the upper left photo represents the typical flowers of the present variety and the upper right photo represents the present variety showing the typical growth habit.

The center photograph displays typical leaves and both the dorsal and ventral coloration thereof is also shown.

On sheet 2, the upper left photo shows the stem (side) view of mature fruits of the present variety with an external coloration sufficiently matured for harvesting and shipment.

Additionally, the upper right photo represents the fruit with a longitudinal sectional view.

In the middle left, the photograph shows the calyx (end) view and the middle right photo represents the transverse view to illustrate the flesh and seed characteristics of the fruit of the present variety.

The bottom center view shows the pips with distinct elongation in shape.

Moreover, a DNA fingerprint of the new variety utilizing Sequence-Based Amplification Polymorphism (SBAP) employing four (4) markers is shown.

DETAILED DESCRIPTION

Referring more specifically to the pomological details of this new and distinct variety of apple tree, the following has been observed under the ecological conditions prevailing at the test orchard which is located at 3539 Road 5 N.W., Ephrata, Wash., and on the original tree located at Alexandra, New Zealand. The major color code designations are by reference to The Royal Horticultural Society, London 1996. Common color names are also employed occasionally.

Tree:

*Size.*—Generally — Average as compared to other apple cultivars. The original tree which is 11 years old is approximately 5 m in height, 4 m in width. Second generation trees are 2 m height and approximately 1.3 m in width.

*Productivity.*—Productive.

*Vigor.*—Moderate.

*Figure.*—Upright, to upright spreading in form.

Trunk:

*Thickness.*—Original tree — 18 cm diameter when measured at 50 cm from the soil surface.

*Surface texture.*—Smooth to furrowed with increasing age. The surface texture was not considered distinctive of the variety.

Branches:

*Size.*—Generally average as compared to other apple cultivars.

*Tree habit.*—Second generation trees, third leaf, branches are about 2–4 cm in diameter. These trees with typically have a 60° crotch angle from central leaders. This is not distinctive of the variety, however.

*Productivity.*—Productive. This is highly dependent on cultural practices, and therefore is not distinctive of the variety.

*Regularity of bearing.*—Regular. The present tree is also considered hardy under the ecological conditions prevailing in the Ephrata, Wash. area.

*Lenticels.*—Numerous small lightly colored greyed-orange (165D) lenticels are normally present over the entire surface area of the trunk. The lenticels range in size from approximately 2 to about 7 millimeters in length, and are approximately 0.1 to about 1 millimeter in height.

*Bark color.*—Generally — Brown, (200C) to a darker brown (200B).

*Surface texture.*—The shoots of the current season's growth are highly pubescent. This pubescence is wooly and gray 201D. This color is not distinctive of the variety.

*Color.*—Two year old wood — Variable. This color ranges from gray-brown (200C) to a darker brown (200B).

*Current season shoots.*—Color — Pale green (130C); and changing to a reddish brown (183D) with advancing senescence.

*Expanding shoot tips.*—Color — Pale green (130B).

*Internode length.*—Considered medium. This length is approximately 15–27 millimeters when measured on young slender shoots.

Leaves:

*Size.*—The leaf size is similar to the 'Gala' and 'Red Delicious' parents with average dimensions as shown below:

*Base shape of leaf.*—Obtuse.

*Length of blade.*—Approximately 10.0 to 10.5 centimeters, including the leaf petiole.

*Leaf width.*—Medium — Approximately 5.5–6.0 centimeters.

*Leaf thickness.*—Medium. This is not a distinctive characteristic of the variety.

*Leaf form.*—Ovate to approaching oval.

*Leaf tip.*—Form — Acute and more typically acuminate.

*Leaf color.*—Upper surface — Variable. Dark green. (139A) to slightly lighter green (137A). Lower surface — Lighter gray-green (139D to 139C).

*Leaf pubescence.*—Upper surface — Lightly pubescent when young and becoming less so with advancing senescence.

*Lower surface.*—Highly pubescent, and having a grayish (201D) appearance which persists even with advancing senescence. This color is not distinctive, however.

*Leaf petiole size.*—Medium in Length. Approximately 25 to 33 millimeters.

*Petiole diameter.*—Variable from approximately 1.5 to 2.5 millimeters when measured at mid-petiole. This measurement often broadens at the base to a width which ranges from approximately 3 to about 6 millimeters.

*Color.*—Variable, depending upon the age and light exposure of the leaf. Young leaves normally appear quite pubescent and light green in color (144B). On occasion, the petioles may be slightly tinged with reddish hues (59B). Older leaves, in contrast, appear slightly darker in color (144A) to occasionally green-yellow (145A). Often these older petioles have a red coloration on the base of the petiole (59B).

*Surface texture.*—Pubescence is persistent on the petiole surface throughout the entire growing season.

*Leaf stipules.*—Size — Approximately 10 mm in length; 1 mm in width; and considered persistant. The stipules (2) are located near the base of the leaf petiole.

*Form.*—Normally, linear lanceolate. As a general matter, small dark trichomes are often present along the stipule margins. The color of these trichomes are not distinctive of the variety.

*Color.*—Immature stipules — These appear pale green in color (144D), and are often tinged with red (61A). Mature stipules have a darker green color (137B) especially apically. Further, the mature stipules may have a yellowish color which is often tinged with red (61A). This red color normally appears basally.

Flowers:

*Blooming time.*—Generally — The blooming time is considered to be mid-season and similar to the 'Gala' and 'Red Delicious' apple cultivars growing in the Columbia Basin of Central Washington.

*Date of full bloom.*—During the 1999 growing season, full bloom was achieved about 30 April. In the 2000 growing season full bloom was achieved on May 5, 2001.

*Chilling requirement.*—The variety appears to have a normal apple chilling requirement. The chilling requirement has not been precisely determined.

*Flower bud (popcorn stage).*—Size — approximately 1 cm in length and width; oblong; and light pink in color (51A). Flower height including the pedicel is about 40–50 mm. Normally 5 flowers per cluster are found. The flowers have a slight fragrance.

*Flower size.*—Generally — Medium to large as compared to other varieties.

*Flower diameter.*—At full expansion, the flowers have a diameter of approximately 43 to 47 millimeters.

*Bloom quantity.*—Generally — Average to abundant.

*Petals.*—Size — Considered large as compared to other varieties.

*Length.*—Approximately 23 to about 28 millimeters.

*Width.*—Approximately 18 to about 21 millimeters.

*Petal number.*—5.

*Petal form.*—Variable. Broadly ovate and occasionally narrowly so.

*Petal color.*—Mature flowers — Both surfaces of the flowers are White, (155B). Prior to full bloom the flowers appear to have a pale pink coloration (66D) which is primarily located on the lower surface. This pink coloration can at times occur in sectors, or occasionally in streaks within the overall white.

*Petal claw.*—Form — Relatively long, tapered and truncated, especially at the base.

*Petal claw length.*—Approximately 2.25 to about 3.25 millimeters.

*Petal claw width.*—Approximately 1 millimeter.

*Petal margins.*—Form — Relatively smooth and having only a slight undulation. As a general matter, the petal margins usually cup inwardly at maturity.

*Flower pedicel.*—Surface texture — The surface of the pedicel is considered highly pubescent.

*Length.*—Moderately long, approximately 15 to 24 millimeters.

*Thickness.*—Approximately 1 millimeter.

*Floral nectaries.*—Color — Pale cream-green (150C).

*Sepals.*—Surface texture — Pubescent, Five.

*Sepal size.*—Medium, and broadly lanceolate and occasionally conic in form. Approximately 12 mm in length and 4 mm in width when measured at base.

*Sepal color.*—Pale green (142C).

*Anthers.*—Size — Approximately 1 mm in length. Color — Buff-yellow (8B).

*Pollen production.*—Abundant.

*Pollen color.*—Light yellow (7C).

*Filaments.*—Length — Variable, from approximately 7 to about 12 millimeters, and appearing slightly shorter than the pistils at full extension.

*Filament color.*—White (155B) when immature.

*Pistil.*—Length — Approximately 12 to about 14 millimeters in length and branching into 5 styles, all of which are fused at the base.

*Pistil color.*—Pale green (142D).

*Surface texture.*—Slightly pubescent basally from the ovary to the style division, and on the basal area of the five individual styles just above the style division. The upper portion of the five styles has a slight pubescence although it may from time-to-time appear glabrous from mid-style to the stigma.

*Bud scales.*—Form — Medium in size and conic in form.

*Surface texture.*—Moderately long and a wooly pubescence is present.

*Bud scales.*—Color — Brownish-gray (197A). Interior color — dark brown (199A).

Fruit:

*Maturity when described.*—The present variety of apple is described as it would be found at full commercial maturity under the ecological conditions prevailing at Ephrata, Wash.

*Date of first pick in* 1999.—About Sep. 9, 1999 — This date of maturity is approximately midway between the parents, 'Gala' and 'Red Delicious'.

*Date of last pick in* 1999.—Sep. 20, 1999.

*Fruit size.*—Generally medium to large. This size is considered midway between the 'Gala' and 'Red Delicious' cultivars growing in the same geographical location and receiving the same cultural practices. Average weight is about 260 grams.

*Uniformity.*—Uniform.

*Average cross sectional diameter.*—Approximately 70 to 90 millimeters.

*Fruit form.*—Generally — Somewhat variable. As a general matter, in the lateral aspect, the fruit produced by the present variety is most frequently oblong to conical in form and distinctly elongated. Further, the overall fruit form is very unique to the fruit variety, and is defined in the trade as "typey".

*Fruit skin.*—Thickness — Medium, and relatively neutral in flavor. Russetting is evident, but is considered very low.

*Fruit skin color.*—Variable. The ground color is a light yellow (151C) to a bright yellow-gold (150A). Over color is a light red (44B). When blushed fruit are found, the blush covers about 10% of the free fruit surface area. The blush is solid with stripes. Some fruit can be colored up to about 90% full red over color (45B).

*Fruit stem.*—Length — Medium to long, approximately 19 to about 28 millimeters.

*Thickness.*—Approximately 2 to about 2.5 millimeters when measured at mid-stem. The stem appears slightly thicker or clubbed, at the distal end.

*Color.*—Light green (141D) with red-purple striping (60B).

*Stem cavity.*—Width — Medium, approximately 28 to 36 millimeters.

*Stem cavity.*—Shape — The stem cavity shoulder is rounded and the cavity surface at times appears russetted.

*Stem cavity depth.*—Approximately 14 to about 20 millimeters.

*Stem cavity depression.*—Shape — Acute, approaching acuminate.

*Fruit basin.*—The basin of the Nevson apple is average in size and relatively wide. The basin shoulders are rounded and usually lobed.

*Fruit basin.*—Surface texture — Smooth. Occasionally, calyx cracks are evident.

*Calyx.*—Size — Approximately 21–28 mm in width; and approximately 14–16 mm in depth.

*Calyx form.*—Fully closed.

*Calyx lobes.*—Generally — These lobes are not prominent on the fruit.

*Calyx tubes.*—Shape — Conical in form, often with the floral stamens persistent in the tube.

*Position.*—Basal, but approaching median.

*Fruit core.*—Size — Average, and usually median in position within the fruit.

*Seed count.*—5 seeds are present.

*Seed.*—Texture — The surface texture of each of the seeds are smooth.

*Color.*—Dark red-brown (175B).

*Seed apex shape.*—The seed apex is acute.

*Flesh color.*—Generally — White (155A) to a very light creamy yellow-green (145D). A few long fibers are evident in the flesh. These vary in color from white to a very pale green.

*Flesh texture.*—Generally — Fine grained, firm, crisp and juicy.

*Flesh pressure.*—Generally speaking, the present variety displays a flesh pressure which is about 2 PSI more than its parent 'Gala'.

*Flesh firmness.*—Storage indications show a longer retention of firmness than the 'Gala' parent.

*Fruit flavor.*—The fruit produced by the present variety of apple tree is sweet, aromatic, and has low acidity. Overall, the fruit is well-balanced and pleasant with a distinctly fruity flavor.

*Diseases.*—The present variety appears subject to "watercore" as it increases in fruit maturity. No other specific resistances or susceptibility to plant/fruit disease has been observed.

*Eating quality.*—Generally — Very good to excellent.

DNA Finger Print

The technique which yielded the DNA Finger Print shown in the drawings was produced by a marker system called Sequence-Based Amplification Polymorphism (SBAP). The four markers employed with the present variety of apple are as follows:

1.) CQ Em1 (5'GACTGCGTACGAATTCAAT-3')

2.) CQ Em2 (5'GACTGCGTACGAATTCTGC-3')

3.) CQm E1 (5'GAGTCCAAACCGGATA-3')

4.) Cqm E2 (5'TGAGTCCAAACCGGAGC-3')

PCR Conditions

5 Cycles comprising denaturing for one minute at 94° C.; annealing for one minute at 35° C.; and extension for one minute at 72° C.

30 Cycles comprising denaturing for 40 seconds at 94° C.; annealing for 40 seconds at 50° C.; and extension for 40 seconds at 72° C.

Although the new variety of apple tree herein denominated as 'Nevson' possesses the described characteristics when grown under the ecological conditions prevailing in the Columbia Basin of Central Washington, it is to be understood that variations of the usual magnitude and characteristics incident to changes in growing conditions, fertilization, pruning, and pest control are to be expected.

Having thus described and illustrated my new variety of apple tree, what I claim as new and desire to secure by Letters Patent is:

1. A new and distinct variety of apple tree substantially as illustrated and described and which is somewhat similar in its harvesting date to the 'Gala' cultivar which matures in approximately the same season, and about 20 days earlier than the common commercial variety 'Golden Delicious', but which is distinguished therefrom, and characterized principally as to novelty by producing an attractively colored red speckled and striped yellow skinned fruit which is ripe for harvesting and shipment approximately September 10 to about October 1 under the ecological conditions prevailing in the Columbia Basin of Central Washington.

* * * * *

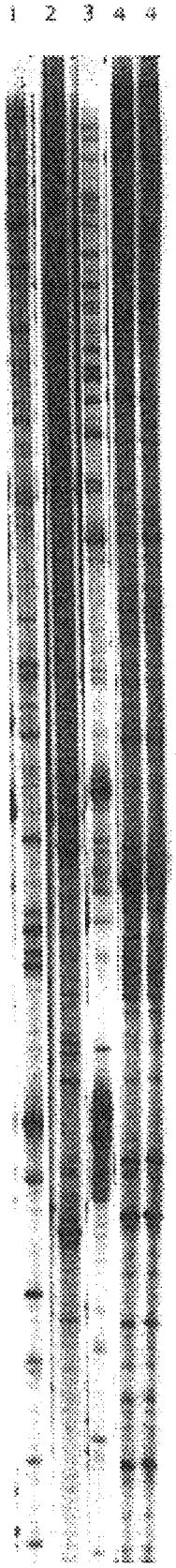
1 2 3 4 4

UNITED STATES PATENT AND TRADEMARK OFFICE

CERTIFICATE OF CORRECTION

PATENT NO. : PP 12,415 P2
DATED : February 19, 2002
INVENTOR(S) : John McLaren

It is certified that error appears in the above-identified patent and that said Letters Patent is hereby corrected as shown below:

Column 7,
Line 29, replace "3.) CQm E1 (5GAGTCCAAACCGGATA-3')" with
-- 3.) CQm E1 (5TGAGTCCAAACCGGATA-3') --.

Signed and Sealed this

Twenty-second Day of October, 2002

*Attest:*

*Attesting Officer*

JAMES E. ROGAN
*Director of the United States Patent and Trademark Office*